United States Patent [19]

Heckert et al.

[11] Patent Number: 5,516,535
[45] Date of Patent: May 14, 1996

[54] BEVERAGE COMPOSITIONS HAVING ENHANCED β-CAROTENE BIOAVAILABILITY

[75] Inventors: David C. Heckert, Oxford; Haile Mehansho, Fairfield; Glenn R. Hudepohl; Samuel Crosby, Jr., both of Cincinnati, all of Ohio

[73] Assignee: The Procter & Gamble, Cincinnati, Ohio

[21] Appl. No.: 192,205

[22] Filed: Feb. 4, 1994

Related U.S. Application Data

[63] Continuation of Ser. No. 978,591, Nov. 19, 1992, abandoned.

[51] Int. Cl.$^6$ ............................. A23L 2/00; A23L 1/30
[52] U.S. Cl. ............................. 426/2; 426/72; 426/73; 426/74; 426/590; 426/599; 426/648
[58] Field of Search ............................. 426/2, 72, 74, 426/590, 648, 599, 73

[56] References Cited

U.S. PATENT DOCUMENTS

| | | | |
|---|---|---|---|
| 695,823 | 5/1991 | Andon et al. | |
| 2,325,360 | 7/1943 | Ayers | 99/155 |
| 3,114,641 | 12/1963 | Sperti et al. | 99/105 |
| 3,657,424 | 4/1972 | Aktins et al. | 424/153 |
| 3,992,555 | 11/1976 | Kovacs | 426/72 |
| 3,992,556 | 11/1976 | Kovacs et al. | 426/72 |
| 4,486,413 | 12/1984 | Wiesenberger | 424/177 |
| 4,497,800 | 2/1985 | Larson et al. | 512/2 |
| 4,710,387 | 12/1987 | Uiterwaal et al. | 426/72 |
| 4,722,847 | 2/1988 | Heckert | 426/74 |
| 4,725,427 | 2/1988 | Ashmead et al. | 424/44 |
| 4,737,367 | 4/1988 | Langer et al. | 426/72 |
| 4,786,510 | 11/1988 | Nakel | 426/74 |
| 4,992,282 | 2/1991 | Mehansho et al. | 426/72 |
| 5,128,374 | 7/1992 | Kochanowski | 514/574 |
| 5,153,012 | 10/1992 | Ohtaka et al. | 426/72 |

FOREIGN PATENT DOCUMENTS

| | | |
|---|---|---|
| 2461772 | 11/1987 | European Pat. Off. |
| 2219778 | 9/1974 | France |
| 56-97248 | 8/1981 | Japan |
| 59-31710 | 2/1984 | Japan |
| 2049719 | 8/1988 | Japan |
| 1262235 | 2/1972 | United Kingdom |
| WO91/19692 | 5/1991 | WIPO |

OTHER PUBLICATIONS

Watt, K. et al. 1975. Composition of Foods, Agriculture Handbook No. 8, Agriculture Research Service, U.S.D.A., pp. 41, 167.

Harinder S. Garenwal, "Potential Role of Beta-Carotene and Antioxidant Vitamins in the Prevention of Oral Cancer", Beyond Deficiency, New Views on the Function and Health Effects of Vitamins (1992).

R. G. Ziegler, "Vegetables, Fruits and Carotenoids and the Risk of Cancer", Am. J. Clin. Nutr., 53, 251s–259s (1991).

J. W. Erdman, Jr. et al. "Factors Affecting the Bioavailability of Vitamin A, Carotenoids, and Vitamin E", Food Technology, 214–221 (1988).

J. G. Bieri, "Are the Recommended Allowances for Dietary Antioxidants Adequate" Free Radical Biology and Medicine, 3, 193–197 (1987).

Ting et al.; "Nutrients and Nutrition of Citrus", Citrus Nutrition & Quality pp. 4–24, *American Chemical Society* (1980).

Erdman et al., "Factors Affecting the Bioavailability of Vitamin A, Carotenoids, and Vitamin E", *Food Technology,* pp. 214–221 (1981).

Erdman et al., "Effects of Purified Dietary Fiber Sources on Beta–Carotene Utilization by the Chick", *J. Nutr.,* pp. 116, 2415–2423 (1985).

Erdman et al., "Effects of Purified Dietary Fiber Sources on Beta–Carotene Utilization by the Chick", J. Nutr., 116, 2415–2423 (1986).

P. Prolux et al., "Interaction of Lipids with Intestinal Brush Border Membrane Preparations", Can. J. Biochem., 60, 7, 904–909 (1982).

F. Weber et al., "Absorption Mechanisms for Fat–Soluble Vitamins and the Effect of Other Food Constituents", Prog. Clinical Biol. Res., 77, 119–135 (1981).

E. W. Strauss et al., "Some Factors Affecting the Lipid Secretory Phase of Fat Adsorption by Intestine In–Vitro from Golden Hamster", J. Lipid Res. 22, 147–156, (1981).

Nagy et al. Citrus Science and Technology, vol. I, Chapter 6, 229, Chapter 8, 302, Chapter 10, 397 (1976).

E. DeRitter, "Stability Characteristics of Vitamins in Processed Foods", Food Technology, (1976).

Rodriguez et al., "A Conspectus of Research on Vitamin A Requirements of Man", J. Nutrition 102, 7, 909–968, (1972).

Goodman et al., "The Intestinal Absorptions and Metabolism of Vitamin A and Beta–Carotene in Man", J. Clin. Invest., 45, 1615–623, (1966).

*Primary Examiner*—Helen Pratt
*Attorney, Agent, or Firm*—Rose Ann Dabek; J. C. Rasser

[57] ABSTRACT

A method for enhancing β-carotene absorption in animals and humans by administering a beverage comprising:

(a) from about 0.05% to about 0.3% calcium;

(b) at least 0.0004% of β-carotene;

(c) about 0.5% to about 60% sweetener;

(d) at least 0.005% flavor; and (e) the remainder being water is disclosed. The beverage can contain vitamin C, A, B, D and E. The beverage must be essentially free of iron and metals which cause vitamin degradation. Preferably the beverage contains gums or thickeners.

22 Claims, No Drawings

BEVERAGE COMPOSITIONS HAVING ENHANCED β-CAROTENE BIOAVAILABILITY

This is a continuation of application Ser. No. 07/978,591, filed on Nov. 19, 1992, abandoned.

TECHNICAL FIELD

The present invention relates methods for enhancing betacarotene bioavailability in beverages containing calcium and beta-carotene

BACKGROUND OF THE INVENTION

Vitamin and mineral supplements for human and veterinary use are commonplace. Vitamin supplementation is important primarily for those who have inadequate diets, including growing children.

Vitamins oxidize or otherwise degrade over time. Orange juice and other citrus beverages lose their vitamin C content during storage. Vitamin C (ascorbic acid) acts as an anti-oxidant and therefore is itself oxidized or changed when added to beverages. Vitamin A and its precursor, β-carotene, and riboflavin are also subject to degradation over time. The amount of beta-carotene absorbed by the body is also dependent on the beverage or vehicle in which it is delivered. A number of additives affect the bioavailability of β-carotene. These include fats and emulsifiers. Relatively high levels of dietary fibers, including hemicellulose and pectin, can also have an effect.

Calcium supplementation is also important for those who restrict their intake of dairy foods due to allergies or cholesterol concerns.

It would be desirable, therefore, to have a beverage containing beta-carotene wherein bioavailability is optimized and which also contained calcium. Surprisingly, it has been found that beta-carotene has enhanced bioavailability when administered with calcium.

It is an object of the present invention to provide mixed vitamin and calcium beverages which fulfill these unmet needs and which are storage stable.

These and other objects are provided herein.

SUMMARY OF THE INVENTION

A method for enhancing β-carotene absorption in animals and humans by administering a beverage comprising:

(a) from about 0.05% to about 0.3% calcium;

(b) at least 0.0004% of β-carotene;

(c) about 0.5% to about 60% sweetener;

(d) at least 0.005% flavor; and (e) the remainder being water.

Vitamin C, A, B, D and E can also be added. The beverage must be essentially free of iron and metals which cause vitamin degradation. Preferably the beverage contains gums or thickeners.

All ratios, proportions and percentages herein are by weight, unless otherwise specified.

DETAILED DESCRIPTION OF THE INVENTION

As used herein, the term "comprising" means various components can be conjointly employed in the beverages of the present invention. Accordingly, the terms "consisting essentially of" and "consisting of" are embodied in the term comprising.

By "nutritional" or "nutritionally-supplemental amount" herein is meant that the vitamin and calcium sources used in the practice of this invention provide at least 10% of the Recommended Daily Allowance (RDA) of the daily intake for vitamins and minerals as defined in the United States (see Recommended Daily Dietary Allowance-Food and Nutrition Board, National Academy of Sciences-National Research Council). The serving used to calculate the RDA is 177 ml or 6 ounces in this application.

The bioavailability of β-carotene from the beverage is believed to be primarily derived from the calcium. However, the addition of gums and carbohydrates plays a role in this effect. The following table illustrates β-carotene bioavailability from various solutions or mixtures. The data is based on animal studies. The procedure is described in detail below.

| Sample | Treatment β-carotene in | Liver Vitamin A Level (μ/g + SEM) |
|---|---|---|
| 1 | Water | 10.12 ± 0.84 |
| 2 | Water + $CaCl_2$ | 13.75 ± 0.99 |
| 3 | Water + CCM | 16.6 ± 1.6 |
| 4 | Example I | 21.5 ± 2.4 |
| 5 | 20% Fruit Juices | 13.5 ± 0.95 |
| 6 | CCM and potassium citrate | 17.68 ± 2.03 |
| 7 | Water + HFCS, sorbitol, gums | 18.32 ± 1.72 |
| 8 | Water + Vitamins E, C and riboflavin | 12.94 ± 1.92 |
| 9 | Water + flavor (including oil and emulsifier) | 15.67 ± 1.07 |

Samples 1, 2 and 3 are based on a different baseline than the other products. Sample 3 was in a different test from Samples 1 and 2.

βCarotene

Encapsulated β-carotene in dextrin is preferred. Other encapsulation agents are starch and gelatin. These materials are acceptable but they may have an effect on the calcium β-carotene interaction. Similar encapsulation materials can also be used. Roche Vitamins and Fine Chemicals, Nutley, N.J. is a source of encapsulated β-carotene (1% and 10% powder). A level of from about 0.0004% or about 0.75 mg/177 gm beverage provides at least 25% of the RDA of vitamin A as β-carotene. Preferably from about 0.0008% to about 0.0085% (50% to about 500% RDA) and, most preferably, from about 0.0017% to about 0.008% β-carotene is used in the beverages, in the practice of this invention, the Recommended Daily Allowance (RDA) of the daily intake for betacarotene (Vitamin A) is defined in the United States (see Recommended Daily Dietary Allowance— Food and Nutrition Board, National Academy of Science National Research Council). The serving used to calculate the RDA is 177 ml or 6 oz. Other sources of β-carotene can also be used. These include oil dispersions and pure β-carotene.

Other vitamins can also be included. Any commercially available source of vitamin C or ascorbic acid can be added to the beverage. Encapsulated vitamin C and edible salts of ascorbic acid can also be used. Preferably from about 25% to about 500% of the RDA is used in the beverages (15 mg/177 gm of finished beverage or 0.0085% to about 300 mg/177 gm of finished beverage or 0.17%). Most preferably, the amount of vitamin C used is from about 0.01% to about 0.15% by the weight.

Commercially available source of riboflavin can be used, preferably from about 20% to about 500% of the RDA in the beverage (0.34 mg/177 ml to 8.5 mg/177 ml of finished beverages).

Other vitamins which can be added to the beverages include vitamin $B_6$, niacin, pantothenic acid, folic acid, vitamin D, vitamin E, vitamin $B_{12}$ and thiamine. These can be added at levels of from 10% to 300% RDA.

Calcium

The calcium is present at from about 0.05% to about 0.3%. For concentrated beverages, from about 0.15% to about 1.0% calcium is used.

Preferred calcium sources are calcium organic acid complexes. The preparation of the preferred calcium source used herein, calcium organic complexes, and preferably, "calcium citratemalate", is described in U.S. Pat. No. 4,786,510 and U.S. Pat. No. 4,786,518 issued to Nakel et al (1988) and U.S. Pat. No. 4,722,847 issued to Heckert (1988); and co-pending application of: Fox et al., Ser. No. 07/537,313 filed Jun. 14, 1990 incorporated herein by reference. A nutritionally supplemental amount of calcium is used.

Other calcium sources include calcium acetate, calcium tartrate, calcium lactate, calcium malate, calcium citrate, calcium phosphate, calcium orotate, and mixtures thereof. Calcium chloride and calcium sulfate can also be included; however at higher levels they taste astringent. Virtually any organic acid salt can be used so long as it is edible and does not provide an off-flavor. The choice of salt or salt mixture will be determined by the solubility and the taste. Citrate, malate and ascorbate yield ingestible complexes whose flavors are judged to be quite acceptable, particularly in fruit juice beverages. Tartaric acid is acceptable, particularly in grape juice beverages, as is lactic acid. Longer-chain fatty acids may be used but can affect flavor and water solubility. For essentially all purposes, the malate (preferred), gluconate, citrate and ascorbate moieties suffice.

Flavor Component

The flavor component of the present invention contains flavors selected from natural flavors, botanical flavors and mixtures thereof. The term "fruit flavors" refers to those flavors derived from the edible reproductive part of a seed plant, especially one having a sweet pulp associated with the seed. Also included within the term "fruit flavor" are synthetically prepared flavors made to simulate fruit flavors derived from natural sources.

The term "botanica flavor" refers to flavors derived from parts of a plant other than the fruit; i.e. derived from bean, nuts, bark, roots and leaves. Also included within the term "botanical flavor" are synthetically prepared flavors made to simulate botanical flavors derived from natural sources. Examples of such flavors include cocoa, chocolate, vanilla, coffee, kola, tea, and the like. Botanical flavors can be derived from natural sources such as essential oils and extracts, or can be synthetically prepared.

The particular amount of the flavor component effective for imparting flavor characteristics to the beverage mixes of the present invention ("flavor enhancing") can depend upon the flavor(s) selected, the flavor impression desired, and the form of the flavor component. The flavor component can comprise at least 0.005% by weight of the beverage composition.

For chocolate or cocoa, the amount of flavor will be from about 0.05% to about 20%. Lower amounts of artificial or synthetic chocolate flavors are used than for cocoa itself. Chocolate beverages can also include whey and milk solids. For the other flavors, the amount added to the beverage will be from about 0.05% to about 10%. If juice is the flavorant, from 5% to 99.95% can be used. Juice also furnishes sugar or sweetener. The amount of flavor added is within the skill of one in the art and depends on the flavor intensity desired.

As used herein, the term "aqueous essence" refers to the water soluble aroma and flavor materials which are derived from fruit juices. Aqueous essences can be fractionated, concentrated or folded essences, or enriched with added components.

As used herein, the term "essence oil" refers to the oil or water insoluble fraction of the aroma and flavor volatiles obtained from juices. Orange essence oil is the oily fraction which separates from the aqueous essence obtained by evaporation of orange juice. Essence oil can be fractionated, concentrated or enriched.

As used herein, the term "peel oil" refers to the aroma and flavor materials obtained by extraction or pressing of the citrus fruit peel. Peel oil and essence oil derived from oranges and other citrus fruits is largely composed of terpene hydrocarbons, e.g. aliphatic aldehydes and ketones, oxygenated terpenes and sesquiterpenes. From about 0.002% to about 1.0% of aqueous essence and essence oil are used in citrus flavored juices.

Any juice can be used to make the beverage of this invention. For example, apple, cranberry, pear, peach, plum, apricot, nectarine, grape, cherry, currant, raspberry, gooseberry, blackberry, blueberry, strawberry, lemon, orange, grapefruit, passion fruit, mandarin, mirabelle, tomato, lettuce, celery, spinach, cabbage, watercress, dandelion, rhubarb, carrot, beet, cucumber, pineapple, custard-apple, cocona, pomegranate, guava, kiwi, mango, papaya, banana, watermelon, lo han guo and cantaloupe can be used. Preferred juices are the citrus juices, and most preferred is orange juice. Of the non-citrus juices, apple, pear, cranberry, strawberry, grape, papaya, mango and cherry are preferred.

If a beverage concentrate is desired, the fruit juice is concentrated by conventional means to from about 20° Brix to about 80° Brix. Beverage concentrates are usually 40° Brix or higher (about 40% to about 75% sugar solids).

Sweetener Component

The sweetener composition is usually a monosaccharide or a disaccharide. These include sucrose, fructose, dextrose, maltose and lactose and invert sugar. Other carbohydrates can be used if less sweetness is desired. Mixtures of these sugars can be used.

In addition to sugar of the present invention can contain other natural or artificial sweeteners. Other suitable sweeteners include saccharin, cyclamates, acetosulfam, mogroside, L-aspartyl-L-phenylalanine lower alkyl ester sweeteners (e.g. aspartame), L-aspartyl-D-alanine amides disclosed in U.S. Pat. No. 4,411,925 to Brennan et al. (1983) L-aspartyl-D-serine amides disclosed in U.S. Pat. No. 4,399,163 to Brennan et al., (1983), L-aspartyl-L-1-hydroxymethyl-alkaneamide sweeteners disclosed in U.S. Pat. No. 4,338,346 to Brand, issued Dec. 21, 1982, L-aspartyl-1-hydroxyethylakaneamide sweeteners disclosed in U.S. Pat. No. 4,423,029 to Rizzi, (1983), L-aspartyl-D-phenylglycine ester and amide sweeteners disclosed in European Patent Application 168,112 to J. M. Janusz, published Jan. 15, 1986, and the like. A particularly preferred sweetener is aspartame.

The amount of the sweetener effective in the beverage mixes of the invention depends upon the particular sweetener used and the sweetness intensity desired. For noncaloric sweeteners, this amount varies depending upon the sweetness intensity of the particular sweetener. For sugar (i.e., sucrose), this amount can be from 10% to 85% (typically from 55% to 70%) by weight. In determining the amount of sugar for beverages of the present invention, any sugar or other sweetener present in the flavor component is also included. Low-calorie sweetener combinations containing a noncaloric sweetener such as aspartame and a sugar, such as corn syrup solids, or sugar alcohols can also be used in beverage mixes. In general, the amount of sweetener will be from about 0.5% to about 85%.

Other Beverage Ingredients

Other minor ingredients are frequently included in beverages. Such ingredients include preservatives such as benzoic acid and salts thereof, sulfur dioxide, butylated hydroxyanisole, butylated hydroxytoluene, etc. Also, typically included are natural or synthetically prepared colors.

Salt, e.g. sodium chloride, and other flavor enhancers can be used to improve the flavor of the beverage.

Gums and other thickeners can also be added. These include guar gum, pectin, cellulose and cellulose derivatives, e.g., carboxymethyl cellulose, xanthan, alginate, propylene glycol alginate, gum acacia and mixtures thereof. Preferably, the beverage herein contains from about 0.003% to about 5% of these gums or thickeners. A preferred thickener system contains from about 0.001% to about 0.1% xanthan gum, from 0.001% to about 0.1% guar gum and from about 0.01% to 0.2% propylene glycol alginate. Another preferred gum mixture is from about 0.01% to about 0.05% carboxymethylcellulose and from about 0.05% to about 0.15% carrageenan, preferably Kappa or Iota, with or without xanthan. Weighting oils and clouding agents can also be used.

Emulsifiers can also be included in the beverage. Any food grade emulsifier can be used. Lecithin is a preferred emulsifier. Other edible emulsifiers include mono and diglycerides of long chain fatty acids, preferably saturated fatty acids, and most preferably, stearic and palmitic acid mono- and diglycerides. Propylene glycol esters are also useful in the beverage mixes.

The present invention encompasses various fiber-supplemented juices and beverages. Beverages can contain a Total Dietary Fiber content (AOAC/Prosky) of from about 0.7 to about 3.0 grams per serving. However, in the 2 to 3 gram range the beverage will be more viscous than other beverages without fiber and also these higher levels may have an effect on bioavailability. Most preferred fiber levels are from 0.7 to 1.2 gm per 177 ml serving or from 0.5% to 1.6% fiber. Citrus fibers, cellulose fiber, pulp, pectin and psyllium can be used. Preferably the fiber is less than 100 microns in size. The beverage can also contain from 1% to 4% (w/w) sensible pulp.

The beverage can also contain green tea solids or flavanols as described in U.S. Pat. No. 4,935,256 issued to Tsai (1990).

Packaging

Once prepared, the beverage products of the present invention can be filled into cans, foil-like containers, cartons, bottles or other appropriate packaging. The single-strength juice products are typically pasteurized or sterilized prior to being filled into the packaging. In the case of juice concentrate products, these products are typically frozen.

Preferably, the packaging materials should be impervious to oxygen and damaging light radiation. Optionally, the beverage can be packed under an inert gas to minimize the oxygen content of any container headspace.

Preferably, the product is kept at a temperature of 30° C. or less during long-term storage. Preferably, frozen beverages are kept at a temperature of from −20° C. to −80° C.

The following non-limiting example illustrates the composition of the present invention.

The juices and beverages herein can be carbonated if desired.

EXAMPLE I.

COMPOSITION OF FRUIT-JUICE BASED BEVERAGE (Cranberry Flavored)

| Ingredient | Percent |
| --- | --- |
| Fruit juice concentrates | 3.38 |
| Xanthan gum | 0.015 |
| Carboxymethylcellulose | 0.03 |
| Citric acid | 0.44 |
| Malic acid | 0.33 |
| Calcium hydroxide | 0.24 |
| High fructose corn syrup* | 9.50 |
| Flavor oils | 0.02 |
| Fruit flavors | 0.43 |
| *Riboflavin | 0.005 |
| Ascorbic acid | 0.138 |
| Vitamin E (50%) | 0.02 |
| *β-carotene (1%) | 0.17 |
| Sorbitol | 1.1 |
| Water | 81.45 |
| Potassium citrate | 0.31 |

*High fructose corn syrup containing 55% fructose is used. β-Carotene from Roche - encapsulated in dextrin.

EXAMPLE II

COMPOSITION OF FRUIT-JUICE BASED BEVERAGE (Grapefruit Flavored)

| Ingredient | Percent |
| --- | --- |
| Fruit Juice concentrates | 4.0 |
| Xanthan gum | 0.015 |
| Carboxymethylcellulose | 0.03 |
| Citric acid | 0.44 |
| Malic acid | 0.33 |
| Calcium hydroxide | 0.24 |
| Potassium Citrate | 0.31 |
| High Fructose Corn Syrup (HFCS 55) | 9.50 |
| Sorbitol | 1.10 |
| Aroma and flavor additives | 0.455 |
| Orange pulp | 0.65 |
| Riboflavin | 0.0005 |
| Ascorbic acid | 0.138 |
| β-carotene (1%) | 0.17 |
| Vitamin E (50%) | 0.02 |
| Carrageenan (Kappa or Iota) | 0.10 |
| Water | 81.454 |

Process for Making the Beverages

The ingredients are mixed in the following order. After each addition, the ingredients are thoroughly mixed.

Step 1. Dissolve citric acid and malic acid in water.

Step 2. Add calcium hydroxide as a slurry in water.

Step 3. Add the following ingredients in the following order:
Potassium citrate
Carboxymethylcellulose (CMC) plus Xanthan gum dissolved in water.
High fructose corn syrup (HFCS).
A blend of the juices.

Step 4. Add the following ingredients in the following order.
Riboflavin.
Ascorbic acid.
β-carotene (1% CWS).

Step 5. Add the following in the following order:
Flavors and oils (aqueous essence, aroma concentrate, flavor, etc.).
Vitamin E as tocopherol acetate (50% type CWS/F).
Carrageenan (Kappa or Iota).
Mix thoroughly after each step.

Methodology for β-Carotene Bioavailability Assay Objective

To determine relative bioavailability of β-carotene from beverage prototypes in Sprague Dawley rats.

Procedure

This is called depletion-repletion assay. It is based on the fact that body vitamin A is stored in the liver. Measuring the gain in liver vitamin A in vitamin A depleted rats has been accepted as a standard method of measuring vitamin A and/or β-carotene relative bioavailability. In brief, the procedure includes:

Depletion

To make the animals vitamin A deficient, male weanling rats are fed a vitamin A deficient semipurified diet for about 8 weeks.

Repletion

The vitamin A depleted rats are randomly assigned to different β-carotene containing test beverages. To avoid diet influence, overnight-fasted rats received a test beverage by gavage for 10 days. At the termination of the repletion period, the level of vitamin A (retinol ester) in the liver was measured by using High Performance Liquid Chromatography (HPLC).

What is claimed is:

1. A method for enchancing β-carotene absorption in animals and humans by administering a beverage consisting essentially of:
   (a) from about 0.05% to 0.3% calcium;
   (b) at least 0.0004% β-carotene;
   (c) about 0.5% to about 60% sweetener;
   (d) at least 0.005% flavor; and
   (e) the remainder being water, said beverage being substantially free of iron and other metals which degrade vitamins.

2. A method according to claim 1 wherein the β-carotene is encapsulated in dextrin, gum acacia, starch, gelatin or mixtures thereof.

3. A method according to claim 2 wherein the sweetener is selected from the group consisting of sucrose, fructose, sorbitol, glucose, high fructose corn syrups and invert sugar and mixtures thereof.

4. A method according to claim 3 wherein the sweetener is an artificial sweetener.

5. A method according to claim 3 wherein the flavor is selected from the group consisting of cherry, pineapple, banana, banana puree, apricot, apple, papaya, mango, citrus, grape, cranberry, lo han guo and mixtures thereof.

6. A method according to claim 1 wherein the calcium is selected from the group consisting of calcium lactate, calcium tartrate, calcium acetate, calcium citrate, calcium malate, calcium chloride, calcium sulfate and mixtures thereof.

7. A method according to claim 6 wherein the calcium is calcium-citrate-malate.

8. A method according to claim 7 wherein the flavor is a mixture of peel oil, aqueous essence and essence oil.

9. A method according to claim 7 wherein the beverage contains from about 25% to about 500% of the RDA of a vitamin selected from the group consisting of vitamin A, vitamin E, vitamin D and riboflavin, niacin, pantotheic acid, folic acid, thiamine and mixtures thereof.

10. A method according to claim 6 wherein said flavor is juice selected from the group consisting of orange, lemon, grapefruit, apple, pear, cranberry, papaya, mango, grape, kiwi, passion fruit, pineapple, apricot, mirabelle, peach, banana, mandarine, and mixtures thereof.

11. A method according to claim 10 wherein said β-carotene is from 0.0004% to 0.0085%.

12. A method according to claim 11 wherein said beverage contains from 1% to about 4% (w/w) sensible pulp.

13. A method according to claim 6 wherein the flavor is orange essence and essence oil.

14. A method according to claim 1 wherein the beverage contains fiber.

15. A beverage according to claim 14 comprising from 0.5% to 1.6% fiber.

16. A method for enhancing the bioavailability of—βcarotene by administering a concentrate consisting essentially of:
   (a) from about 0.15% to about 1.0% calcium
   (b) at least 0.018% β-carotene;
   (c) from 1% to about 60% sweetener;
   (d) an effective amount of flavor; and
   (e) the remainder being water, said concentrate being substantially free of iron and other metals which degrade vitamins.

17. A method according to claim 16 wherein the flavor is from about 0.002% to about 3% added aqueous and oil essences or other flavorants.

18. A method according to claim 17 wherein said juice is selected from the group consisting of citrus juices, apple juice, pear juice, cranberry juice and mixtures thereof.

19. A beverage for providing bioavailable β-carotene consisting essentially of:
   (a) from about 0.05% to about 0.3% calcium;
   (b) at least 0.0004% β-carotene;
   (c) from 0.5% to about 60% added sweetener;
   (d) at least 0.01% flavor; and
   (e) the remainder being water, said beverage being substantially free of iron and other metals which degrade vitamins.

20. A beverage according to claim 19 which additionally comprises from about 0.03% to about 5% gums.

21. A beverage according to claim 20 wherein the gums consist of from about 0.001% to about 0.1% xanthan gum, from about 0.001% to about 0.1% guar gum and from 0.01% to 0.2% propylene glycol alginate.

22. A beverage according to claim 20 which additionally comprises a gum selected from the group consisting of from about 0.01% to 0.05% carboxymethylcellulose, of from about 0.05% to about 0.15% carrageenan, 0.001% to about 0.1% xanthan gum and mixtures thereof.

* * * * *